United States Patent
Bussek

(10) Patent No.: US 8,744,594 B2
(45) Date of Patent: Jun. 3, 2014

(54) ELECTROMEDICAL DEVICE FOR THE NON-INVASIVE REDUCTION OR REMOVAL OF SUBCUTANEOUS ADIPOSE TISSUE

(75) Inventor: Karlheinz Bussek, Deubach (DE)

(73) Assignee: Zimmer MedizinSysteme GmbH, Neu-Ulm (DE)

( * ) Notice: Subject to any disclaimer, the term of this patent is extended or adjusted under 35 U.S.C. 154(b) by 0 days.

(21) Appl. No.: 13/248,163

(22) Filed: Sep. 29, 2011

(65) Prior Publication Data

US 2012/0078326 A1 Mar. 29, 2012

(30) Foreign Application Priority Data

Sep. 29, 2010 (DE) .......................... 10 2010 041 649

(51) Int. Cl.
*A61N 1/06* (2006.01)
*A61B 18/18* (2006.01)
*A61N 1/40* (2006.01)
*A61B 18/12* (2006.01)
*A61B 18/00* (2006.01)

(52) U.S. Cl.
CPC ....... *A61B 18/1815* (2013.01); *A61B 2018/126* (2013.01); *A61N 1/06* (2013.01); *A61B 2018/0016* (2013.01); *A61B 18/18* (2013.01); *A61B 2018/1838* (2013.01); *A61N 1/403* (2013.01); *A61B 2018/00464* (2013.01)
USPC ......................................... 607/101

(58) Field of Classification Search
USPC ................................. 607/100–102
See application file for complete search history.

(56) References Cited

U.S. PATENT DOCUMENTS

| | | | |
|---|---|---|---|
| 5,143,063 A | 9/1992 | Fellner | |
| 5,507,790 A | 4/1996 | Weiss | |
| 6,413,255 B1 * | 7/2002 | Stern | 606/41 |
| 6,463,336 B1 | 10/2002 | Mawhinney | |
| 2006/0265034 A1 * | 11/2006 | Aknine et al. | 607/101 |
| 2008/0183251 A1 * | 7/2008 | Azar et al. | 607/101 |
| 2009/0221999 A1 | 9/2009 | Shahidi | |
| 2010/0217253 A1 | 8/2010 | Mehta | |

FOREIGN PATENT DOCUMENTS

| | | |
|---|---|---|
| JP | H0-1115370 | 5/1989 |
| JP | 2010-511459 | 4/2010 |
| KR | 2010-0105669 | 9/2010 |
| WO | WO 2007/141874 A1 | 12/2007 |

* cited by examiner

*Primary Examiner* — Amanda Patton
(74) *Attorney, Agent, or Firm* — Erik G. Swenson; Fulbright & Jaworski L.L.P.

(57) ABSTRACT

An electromedical device for the non-invasive reduction or removal of subcutaneous adipose tissue, comprising an energy source which provides a high-frequency alternating current, comprising at least two individual emitters which are fed by the energy source and which are designed to emit high-frequency electromagnetic waves into subcutaneous adipose tissue, and comprising a directivity control which is coupled with the individual emitters and which controls the individual emitters in such a way that, by direction and field concentration of the high-frequency electromagnetic waves emitted by the individual emitters, a total electromagnetic field with a desired field geometry can be produced in the subcutaneous adipose tissue.

13 Claims, 5 Drawing Sheets

ELECTROMEDICAL DEVICE FOR THE NON-INVASIVE REDUCTION OR REMOVAL OF SUBCUTANEOUS ADIPOSE TISSUE

FIELD OF THE INVENTION

The invention relates to an electromedical device for the non-invasive reduction or removal of subcutaneous adipose tissue.

BACKGROUND OF THE INVENTION

In overweight persons, excess adipose tissue is nowadays mostly removed by surgery, for example by liposuction. In such surgery, adipose cells are removed from the chosen sites beneath the skin by suction using hollow needles. Such invasive therapeutic procedures of plastic surgery always involve a certain risk, however, in so far as complications occur during the operation and during subsequent healing.

U.S. Pat. No. 5,143,063 discloses a method of removing fatty tissue by focusing microwaves onto the adipose tissue to be removed. In this method, a focusing device in the form of a parabolic reflector is used for field concentration. The use of parabolic reflectors as individual emitters requires a highly material- and cost-intensive production process for the electromedical device, in particular when the device is to have a plurality of individual emitters. Furthermore, the use of parabolic reflectors as the focusing device places limitations on the focusing and concentration ability of the described apparatus, which do not correspond to the requirements desired in a medical application.

Publication U.S. Pat. No. 5,507,790 discloses a method for the non-invasive removal of adipose tissue. In this publication, adipose tissue that is to be removed is irradiated using microwave lenses for focusing. In addition to this apparatus, which is based on complex microwave optics, medicaments having a metabolic action are also used and are intended to generate increased lipid metabolism. A reduction in the volume of the adipose cells is thereby achieved without causing cell death of the adipose cells. The complex microwave optics that is used has microwave lenses, which are known to be of low quality and to have a high optical aberration. These properties prevent the microwave radiation that is used from being focused in an advantageous manner in terms of an effective treatment, because the emitted radiation can be limited to the desired treatment region only with difficulty.

SUMMARY OF THE INVENTION

The invention provides a solution to remove or reduce excess subcutaneous adipose tissue non-invasively in a simple manner.

The invention provides an electromedical device comprising: an electromedical device for the non-invasive reduction or removal of subcutaneous adipose tissue, comprising an energy source which provides a high-frequency alternating current, comprising at least two individual emitters which are fed by the energy source and are designed to emit high-frequency electromagnetic waves into subcutaneous adipose tissue, and comprising a directivity control which is coupled with the individual emitters and which controls the individual emitters in such a way that, by direction and field concentration of the high-frequency electromagnetic waves emitted by the individual emitters, a total electromagnetic field with a desired field geometry can be produced in the subcutaneous adipose tissue.

The idea behind the invention is to control the single individual emitters of the electromedical device according to the invention in a simple manner so that the total electromagnetic field can be matched in the best possible manner to the body shapes of the persons to be treated. Complex mechanical adjustment procedures for the electromedical device are advantageously unnecessary. A controlled and targeted local heating of the tissue leads to the desired reduction or removal of subcutaneous adipose tissue.

Advantageous embodiments and further developments are subject of the further dependent claims and of the description in conjunction with the figures of the drawings.

According to a further development, the electromedical device has individual emitters which are arranged substantially in the form of a matrix and/or in the form of a cascade. In the case of an arrangement of the individual emitters in cascade form, the individual emitters are connected in series or are interlinked in succession. In the case of an arrangement of the individual emitters in matrix form, the individual emitters are arranged relative to one another and interconnected in an array, i.e. in rows and columns.

By means of the arrangement of the individual emitters in matrix or cascade form, the production of a large number of field geometries of different forms is possible in a simple manner. Furthermore, it is possible to change promptly between these field geometries, as required, by a simple and suitable control of the individual emitters of the electromedical device.

According to a further embodiment, at least one of the individual emitters is in the form of a dipole antenna. By configuring the individual emitter as a dipole, a desired emission geometry of the individual emitter can be achieved.

According to a further embodiment, at least one of the dipole antennae is in the form of a $\lambda/2$ dipole or $\lambda$ dipole. As a result, different individual geometries of the electric field can be produced by each of the plurality of individual emitters of the device according to the invention.

According to a further embodiment, at least one of the individual emitters is in the form of a point-type emitter. As a result, a particularly simple and inexpensive construction of the electromedical device can be achieved.

According to a further embodiment, the individual emitters are each oriented in such a way that the individual emitters emit the electromagnetic waves they produce in the same direction. In particular, it can thus be ensured that the individual emitters emit the emitted electromagnetic field in the direction of the body of a person to be treated. The same direction is thus assigned based on how and in what manner the device according to the invention is applied to the person, i.e. is attached to the person. The direction of the application of the device accordingly also determines the assigned direction.

According to a further embodiment, the control device is designed to change the frequencies and/or the amplitude and/or the power of the emitted electromagnetic waves of an individual emitter.

As already stated above, the electromagnetic field is varied by the device according to the invention. The electromagnetic field is thereby changed in particular in terms of its intensity and extent as well as its homogeneity. This change can be changed in a simple manner by varying the frequency, the amplitude and/or the power of the emitted electromagnetic waves of the individual emitter. In this manner, the electromagnetic field can be precisely adapted according to the depth at which the subcutaneous adipose tissue is present in the body of a person to be treated and according to the density and consistency of the adipose tissue.

According to a further embodiment, the control device has at least one delay element. A delay element is arranged to change the electromagnetic field produced by an individual emitter by changing a respective signal propagation time of the control signal. By varying and suitably adapting the signal propagation times of the various individual emitters, the total electromagnetic field can thus be established as required.

According to a further embodiment, a control element has at least one phase shifter. A phase shifter is arranged to change the respective electromagnetic field of the individual emitters by changing its respective phase. This measure also makes it possible to change the geometry of the total electromagnetic field as required.

According to a further embodiment, the device is designed to work in the frequency range from 0.4 to 61.5 GHz, preferably from 1.0 to 7.5 GHz, and particularly preferably from 1.6 to 5.9 GHz, and in particular from 2.4 to 2.5 GHz. By using different frequency ranges it is possible, within the context of fat removal or fat reduction, to use the radiation that achieves the best possible absorption behaviour of the radiation in the region to be treated.

The above embodiments and further developments can, where expedient, be combined with one another as desired. Further possible embodiments, further developments and implementations of the invention also include combinations of the features of the invention described above or below in connection with the implementation examples which have not been mentioned explicitly. In particular, the person skilled in the art will also add individual aspects as improvements or additions to the basic form of the present invention.

BRIEF DESCRIPTION OF THE INVENTION

The present invention is explained in more detail in the following by means of the embodiments shown in the schematic figures of the drawings, in which.

DETAILED DESCRIPTION OF THE INVENTION

Figure 1A:
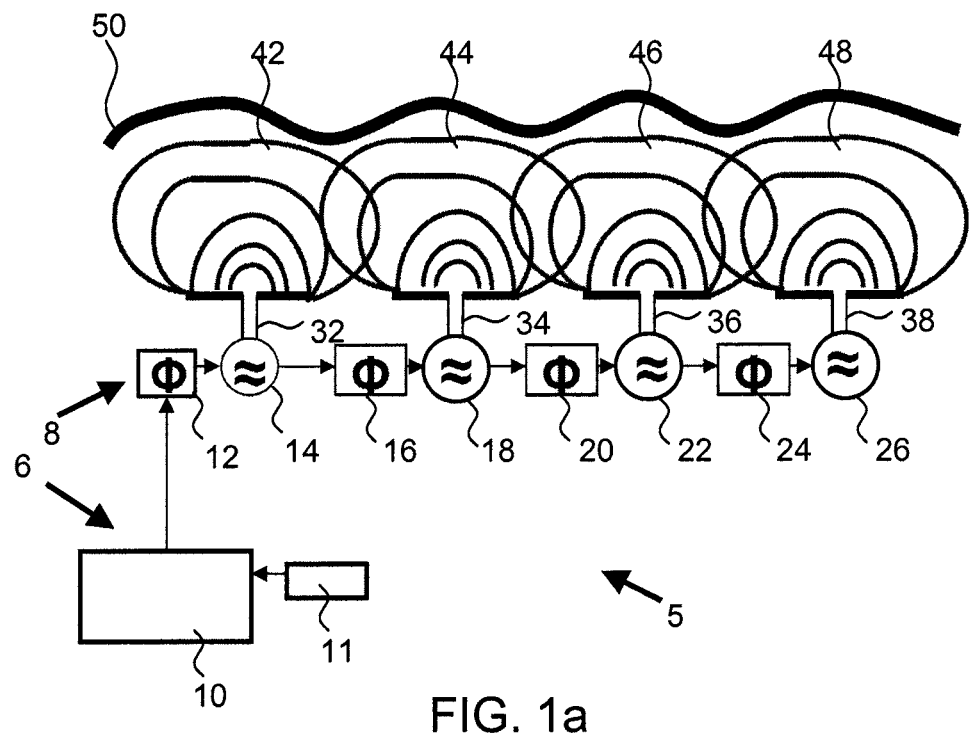
FIG. 1a is a schematic drawing of an embodiment of a device according to the invention.

In the figures, the same reference numerals denote elements, signals and components which are the same or have an equivalent function—unless indicated otherwise.

FIG. 1a is a schematic drawing of the structure of an embodiment of an electromedical device 5 for the non-invasive reduction or removal of subcutaneous adipose tissue, according to a first embodiment of the present invention.

The electromedical device 5 comprises a base part 6, which comprises a directivity control 10 and an energy source 11. The electromedical device 5 further comprises an expansion part 8, which is composed of further subsidiary devices with variable composition of its structure in, for example, cascade or matrix form.

The directivity control 10 is electrically connected on the one hand to the energy source 11 and on the other hand, for example, to a first control element 12. The first control element 12 is further coupled via a first control device 14 to a first individual emitter 32. Further, a second control element 16 is also connected to the first control device 14, and is in turn coupled with a second control device 18. The second control device 18 has, in addition to this connection, a connection on the one hand to a second individual emitter 34 and on the other hand to a third control element 20. The third control element 20 is further connected to a third control device 22, and the third control device 22 is additionally coupled with a third individual emitter 36 and with a fourth control element 24. The fourth control element 24 is in turn connected to a fourth control device 26. The fourth control device 26 is connected to a fourth individual emitter 38. In FIG. 1, four individual emitters with corresponding control devices and control elements are shown by way of example—it will be appreciated, however, that any other number of individual emitters is also possible.

The energy source 11 supplies the electromedical device 5 with energy via the directivity control 10. The directivity control 10 further feeds a high-frequency signal into the first control element 12. The first control element 12 then feeds a high-frequency signal into the first control device 14, in which the high-frequency signal is divided. A first portion of the high-frequency signal is intended for emission via the first individual emitter 32. A second portion of the high-frequency signal is fed from the first control device 14 via the second control element 16 into the second control device 18, in which it is again divided into a portion intended for emission via the second individual emitter 34 and a portion intended for transmission to the third control element 20. The third control element 20 feeds the high-frequency signal onwards into the third control device 22. The third control device feeds a signal for emission into the third individual emitter 36 and transmits a signal to the fourth control element 24. The fourth control element 24 supplies the fourth control device 26, which feeds the fourth individual emitter 38 for emission.

By means of the present cascading of the control elements 12, 16, 20, 24 and of the control devices 14, 18, 22, 26, each individual emitter 32, 34, 36, 38 is supplied individually with a high-frequency signal which is controllable and, in particular, can be varied in terms of phase and frequency. This cascading of control elements and control devices in conjunction with the directivity device 10 permits the formation according to the invention of a desired field geometry of the total electromagnetic field 50, which is formed by the superposition of the electromagnetic fields 42, 44, 46, 48 emitted by each of the individual emitters 32, 34, 36, 38.

The individual emitters 32, 34, 36, 38 can each be in the form of a dipole antenna, in particular in the form of a λ/2 dipole antenna, in the form of a λ dipole antenna or in the form of a 3λ/2 dipole antenna. The directional characteristics of such exemplary antenna forms for the individual emitters are explained in greater detail in the following with reference to FIGS. 2 to 4.

The first control element 12 can comprise, for example, a delay element and/or a phase shifter, the delay element being intended to change the propagation time of the fed-in high-frequency signal, and the phase shifter being designed to change the phase of the fed-in high-frequency signal. The same is true of the control elements 16, 20 and 24.

The control devices 14, 18, 22, 26 are coupled with the individual emitters 32, 34, 36, 38. Furthermore, the control devices 14, 18, 22, 26 are preferably intended to be able to change the high-frequency signals fed to the individual emitters in terms of their frequency and/or power.

Figure 1B:
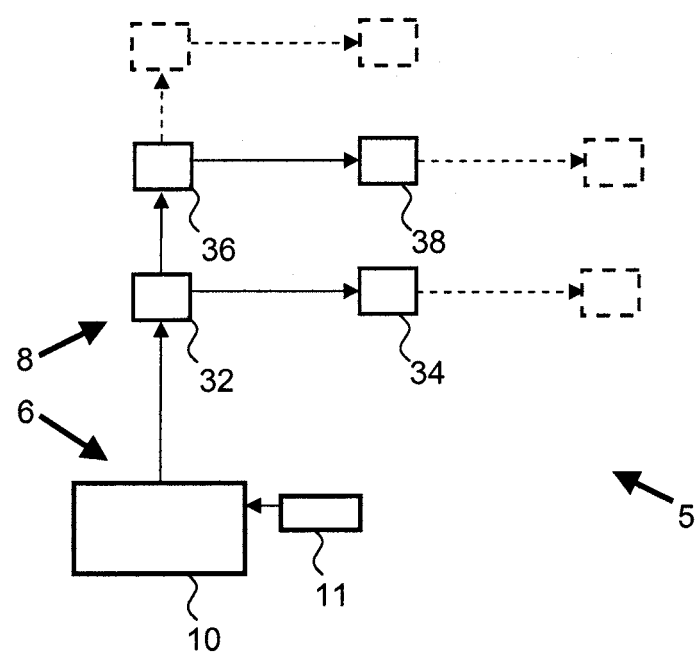
FIG. 1b is a schematic drawing of a further embodiment of a device according to the invention.

FIG. 1*b* is a schematic drawing of an electromedical device according to a further embodiment of the invention. The electromedical device 5, as in FIG. 1*a*, comprises an energy source 11 and a directivity control 10, which can be arranged in a base part 6. The electromedical device 5 further comprises individual emitters 32, 34, 36, 38, which are coupled with the directivity control 10 and are supplied with energy by the energy source 11. As is shown in FIG. 1*b*, the individual emitters 32 and 34 and the individual emitters 36 and 38 are in each case coupled behind one another in a horizontal arrangement in the manner of a cascade. The cascades of the individual emitters 32 and 34 and of the individual emitters 36 and 38 are in each case arranged vertically above one another in a matrix. The present arrangement of the individual emitters 32, 34, 36, 38 is only of exemplary nature. Of course, other cascade and matrix arrangements are possible, for example with cascade rows which are arranged offset above one another or with cascade rows which have a different number of individual emitters. In FIG. 1*b*, therefore, for the purpose of illustration, further individual emitters which can be provided in addition to the individual emitters 32, 34, 36, 38 are shown in dotted lines. The number of individual emitters is shown as four in FIG. 1*b*, but any desired number of individual emitters from two upwards can equally be used.

Figure 2:
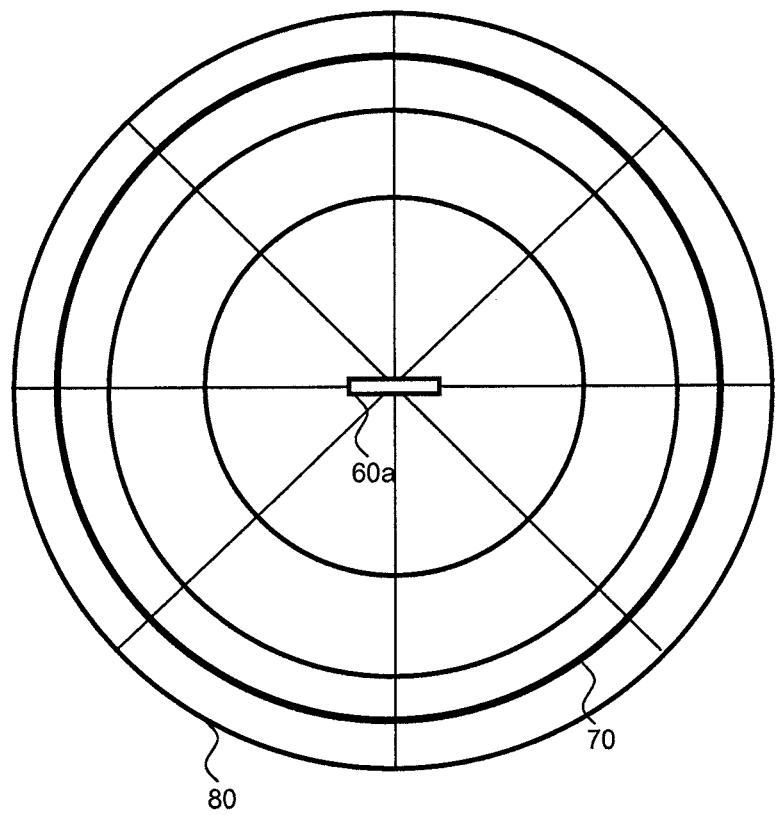
FIG. 2 shows the directional characteristic of a λ/2 dipole in a polar diagram, as produced by means of a device according to the invention.

FIG. 2 is a schematic diagram of the directional characteristic of a $\lambda/2$ dipole in a polar diagram, according to a first embodiment of the present invention.

The directional characteristic of a $\lambda/2$ dipole plotted in a polar coordinate system 80 has an omnidirectional characteristic 70 and depends on the dimensions of the individual emitter in relation to the wavelength of the emitted radiation, and its shape can be adjusted by changing the frequency. In the case of the $\lambda/2$ dipole 60*a*, there is no directivity of the directional characteristic.

Figure 3:
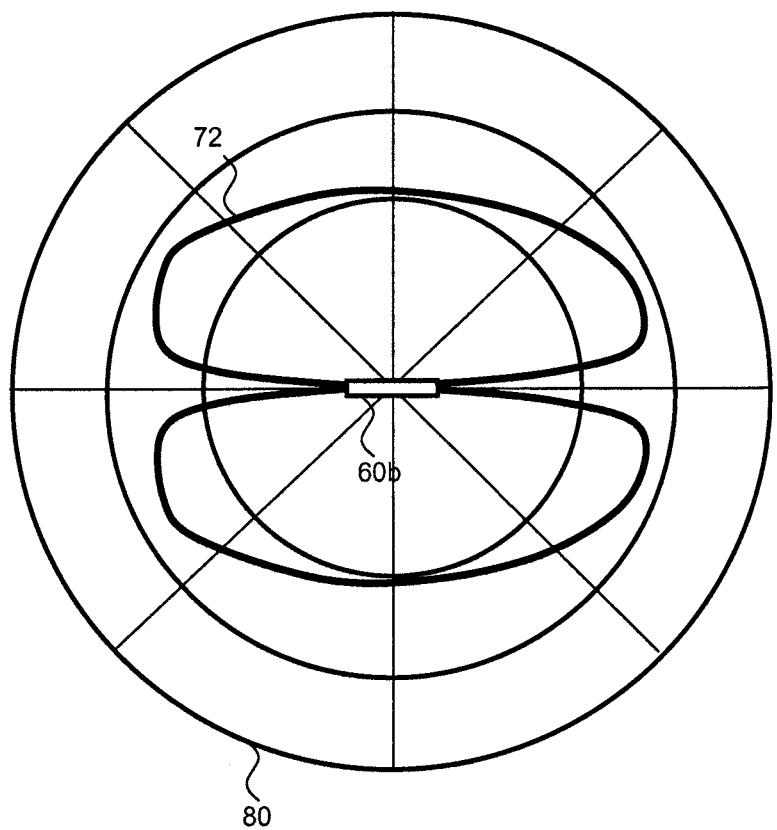
FIG. 3 shows the directional characteristic of a λ dipole in a polar diagram, as produced by means of a device according to the invention.

FIG. 3 is a schematic diagram of the directional characteristic of a $\lambda$ dipole in a polar diagram, according to a first embodiment of the present invention.

The directional characteristic of a $\lambda$ dipole shown in a polar coordinate system 80 has a figure-of-eight characteristic 72 and is dependent on the dimensions of the individual emitter in relation to the wavelength of the emitted radiation, and its shape can be adjusted by changing the frequency. In the case of the $\lambda$ dipole 60*b*, there is directivity of the directional characteristic with emission maxima perpendicular to the dipole axis.

Figure 4:
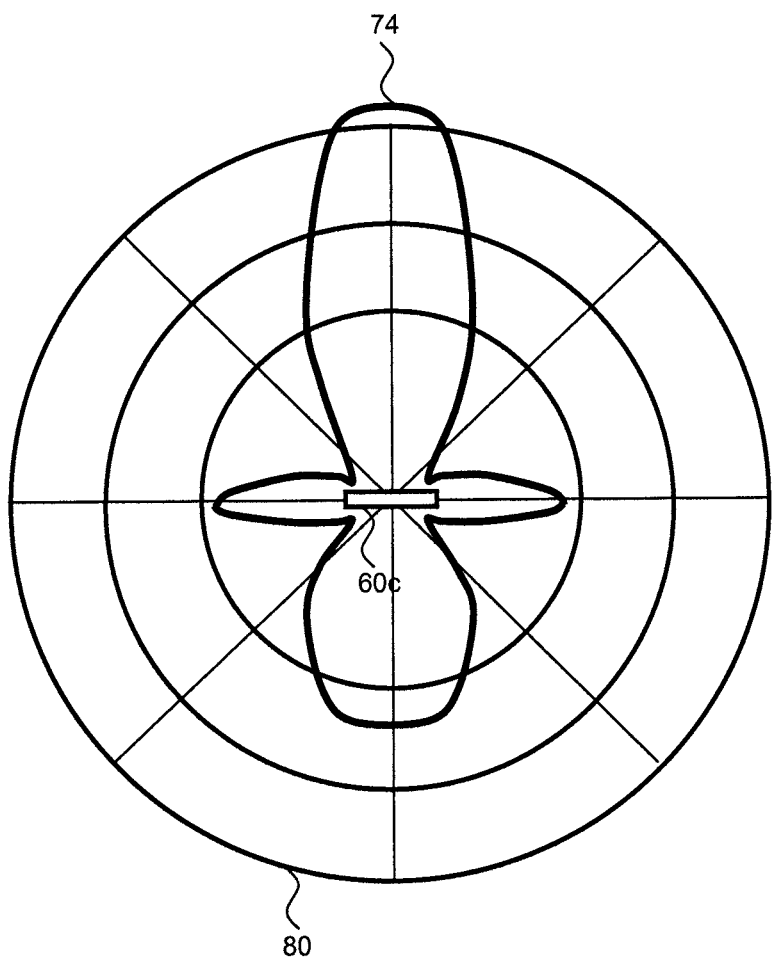
FIG. 4 shows the directional characteristic of a 3λ/2 dipole in a polar diagram, as produced by means of a device according to the invention.

FIG. 4 is a schematic diagram of the directional characteristic of a $3\lambda/2$ dipole in a polar diagram, according to a first embodiment of the present invention.

As can be seen in FIG. 4, the directional characteristic of a $3\lambda/2$ dipole plotted in a polar coordinate system 80 has a unidirectional characteristic 74 and is dependent on the structural form of the individual emitter in relation to the wavelength of the emitted radiation, and its shape can be adjusted by changing the frequency. In the case of the $3\lambda/2$ dipole 60*c*, there is directivity of the directional characteristic with emission maxima in each case orthogonally and parallel to the dipole axis.

Figure 5:
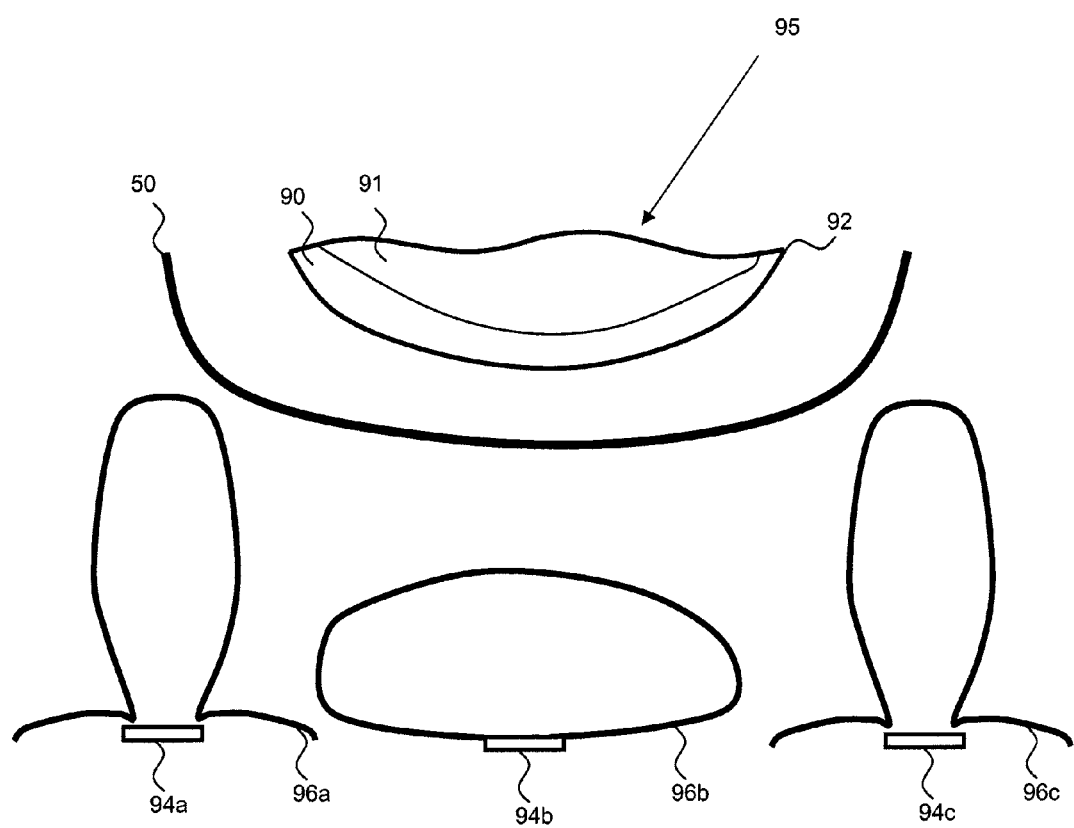
FIG. 5 shows a human tissue region and its spatial position relative to a total electromagnetic field which is produced by three dipole antennae of the device according to the invention.

FIG. 5 is a schematic drawing of a human tissue region and its spatial position relative to the total electromagnetic field 50, which is produced by three dipole antennae of the electromedical device according to the invention, according to a first embodiment of the present invention.

A first dipole antenna 94*a*, a second dipole antenna 94*b* and a third dipole antenna 94*c* produce, by superposition of their different directional characteristics 96*a*, 96*b*, 96*c*, a matched total electromagnetic field 50. In the embodiment shown according to FIG. 5, the second dipole antenna 94*b* is operated as a $\lambda$ dipole, while the first dipole antenna 94*a* and the third dipole antenna 94*c* are connected as $3\lambda/2$ dipoles. The field geometry achieved by the adaptation according to the invention can advantageously be specified by the contour of the human tissue region 95 that is to be treated. It will be appreciated that, according to the tissue region 95, different field geometries are possible by way of different combinations of individual emitters configured as different antennae.

As can be seen in FIG. 5, the power of the dipole antennae 94*a*, 94*b*, 94*c* is further matched to a desired penetration depth of the total electromagnetic field 50 into the adipose tissue 90. The total electromagnetic field 50 thus penetrates the epidermis 92 without penetrating too deep into the muscle tissue 91.

List of Reference Numerals
Electromedical device 5
Base part 6
Expansion part 8
Directivity control 10
Energy source 11
Control device 14, 18, 22, 26
Control element 12, 16, 20, 24
First individual emitter 32
Second individual emitter 34
Third individual emitter 36
Fourth individual emitter 38
Electromagnetic field 42, 44, 46, 48
Total electromagnetic field 50
$\lambda/2$ dipole 60*a*
$\lambda$ dipole 60*b*
$3\lambda/2$ dipole 60*c*
Omnidirectional characteristic 70
Figure-of-eight characteristic 72
Unidirectional characteristic 74
Polar coordinate system 80
Adipose tissue 90
Muscle tissue 91
Epidermis 92
First dipole antenna 94*a*
Second dipole antenna 94*b*
Third dipole antenna 94*c*
Human tissue region 95
First directional characteristic 96*a*
Second directional characteristic 96*b*
Third directional characteristic 96*c*

What is claimed is:

1. An electromedical device for the non-invasive reduction or removal of subcutaneous adipose tissue, comprising:
    an energy source which provides a high-frequency alternating current;
    at least a first individual emitter and a second individual emitter which are fed by the energy source and which are designed to emit high-frequency electromagnetic waves into subcutaneous adipose tissue; and
    a directivity control which is coupled with the individual emitters and which controls the individual emitters in such a way that, by direction and field concentration of the high-frequency electromagnetic waves emitted by the individual emitters, a total electromagnetic field with a desired field geometry can be produced in the subcutaneous adipose tissue, wherein the energy source provides a high-frequency alternating current to the directivity control, and wherein a control device is provided for each individual emitter and is designed to change the frequencies, the amplitude, and the power of the emitted electromagnetic waves of each individual emitter, at least a first control element and a second control element, wherein the directivity control feeds a high-frequency signal into the first control element, wherein the first control element feeds the high-frequency signal into a first control device provided for the first individual emitter, wherein in the first control device the high-frequency signal is divided such that a first portion of the high-frequency signal is fed from the first control device to the first individual emitter for emission and further divided such that a second portion of the high-frequency signal is fed from the first control device via the second control element into a second control device provided for the second individual emitter, and wherein by the second control device the second portion of the high-frequency signal is fed at least in part to the second individual emitter for emission.

2. The device of claim 1, wherein the individual emitters are arranged relative to one another in the form of a cascade or in the form of a matrix.

3. The device of claim 2, wherein the individual emitters arranged in the form of a cascade or in the form of a matrix have a cascade or matrix form such that the desired field geometry can be produced.

4. The device of claim 1, wherein at least one of the individual emitters is in the form of a dipole antenna.

5. The device of claim 4, wherein at least one of the dipole antennae is in the form of a $\lambda/2$ dipole or $\lambda$ dipole.

6. The device of claim 1, wherein at least one of the individual emitters is in the form of a point-type emitter.

7. The device of claim 1, wherein the individual emitters are each oriented in such a way that the individual emitters emit the electromagnetic waves they produce in the same direction.

8. The device of claim 1, wherein the control device has at least one delay element, a delay element being arranged to change the electromagnetic field of an individual emitter by changing a respective signal propagation time.

9. The device of claim 1, wherein a control element which has at least one phase shifter is provided for each individual emitter, a phase shifter being arranged to change the electromagnetic field of the individual emitter by changing its respective phase.

10. The device of claim 1, wherein the device is designed to work in the frequency range from 0.4 to 61.5 GHz.

11. The device of claim 1, wherein the device is designed to work in the frequency range from 1.0 to 7.5 GHz.

12. The device of claim 1, wherein the device is designed to work in the frequency range from 1.6 to 5.9 GHz.

13. The device of claim 1, wherein the device is designed to work in the frequency range from 2.4 to 2.5 GHz.

* * * * *